United States Patent [19]
Savord

[11] Patent Number: 6,013,032
[45] Date of Patent: Jan. 11, 2000

[54] BEAMFORMING METHODS AND APPARATUS FOR THREE-DIMENSIONAL ULTRASOUND IMAGING USING TWO-DIMENSIONAL TRANSDUCER ARRAY

[75] Inventor: Bernard J Savord, Andover, Mass.

[73] Assignee: Hewlett-Packard Company, Palo Alto, Calif.

[21] Appl. No.: 09/039,050

[22] Filed: Mar. 13, 1998

[51] Int. Cl.[7] .................................................... A61B 8/00
[52] U.S. Cl. .......................... 600/443; 600/447; 600/459; 128/916
[58] Field of Search .................................. 600/437, 443, 600/446, 447, 459; 128/916; 73/625, 626; 364/413.25; 367/140

[56] References Cited

U.S. PATENT DOCUMENTS

| | | | |
|---|---|---|---|
| 4,662,223 | 5/1987 | Riley et al. | 73/626 |
| 5,027,820 | 7/1991 | Pesque | 128/660.07 |
| 5,229,933 | 7/1993 | Larson, III | 364/413.25 |
| 5,267,221 | 11/1993 | Miller et al. | 367/140 |
| 5,301,168 | 4/1994 | Miller | 600/447 |
| 5,469,851 | 11/1995 | Lipschutz | 600/447 |
| 5,555,534 | 9/1996 | Maslak et al. | 367/135 |
| 5,573,001 | 11/1996 | Petrofsky et al. | 128/661.01 |
| 5,581,517 | 12/1996 | Gee et al. | 367/138 |
| 5,590,658 | 1/1997 | Chiange et al. | 128/661.01 |
| 5,676,147 | 10/1997 | Petrofsky et al. | 600/447 |
| 5,685,308 | 11/1997 | Wright et al. | 600/443 |

OTHER PUBLICATIONS

Ming Shu et al, "Tricuspid Velocity Profiles Reflect Right Ventricular Diastolic Wall MOtion Abnormalities: Real–Time 3D Echocardiography and Computational Fluid Dynamics", 70th Scientific Session American Heart Assn. Meeting, Nov. 11, 1997, p. 2990.

Takahiro Shiota et al, "Application of a New Real–Time Three–Dimensional Method for Evaluating Right Ventricular Stroke Volume", 70th Scientific Session American Heart Assn. Meeting, Nov. 11, 1997, p. 1830.

Richard L. Goldberg et al, "Multilayer Piezoelectric Ceramics for Two–Dimensional Array Transducer", IEEE Trans. on Ultrasonics, Ferroelectrics & Freq. Control, vol. 41, No. 5, Sep. 1994, pp. 761–771.

Takahiro Ota et al, Novel Determination of Left Ventricular Vol. by Tracing Arbitrary Planes Using Real–Time, 3D Echocardiography: In Vitro and In Vivo Validation, 70th Scientific Session American Heart Assn. Meeting, Nov. 11, 1997, p. 1832.

Takahiro Ota et al, "Accuracy of Left Ventricular Stroke Volume Measurement Using Real–Time, Three Dimensional Echocardiography & Electromagnetic Flow Probe in Vivo", 70th Scientific Seesion American Heart Assn. Meeting, Nov. 11, 1997, p. 1831.

Craig E. Fleishman et al, "Evaluation of Atrioventricular Valve Abnormalities Using Real–Time Three–Dimensional Echocardiography", 70th Scientific Session American Heart Assn. Meeting, Nov. 11, 1997, p. 1045.

*Primary Examiner*—Marvin M. Lateef
*Assistant Examiner*—Ali M. Imam

[57] ABSTRACT

An ultrasound imaging system includes a two-dimensional array of ultrasound transducer elements that define multiple subarrays, a transmitter for transmitting ultrasound energy into a region of interest with transmit elements of the array, a subarray processor and a phase shift network associated with each of the subarrays, a primary beamformer and an image generating circuit. Each subarray processor includes receive circuitry responsive to transducer signals generated by receive elements of the associated subarray for providing first and second subarray signals. The first subarray signal comprises a sum of first component signals, and the second subarray signal comprises a sum of second component signals. The first and second component signals are derived from the respective transducer signals. The phase shift network phase shifts and combines the first and second subarray signals to provide a phase shifted subarray signal. The primary beamformer delays each of the phase shifted subarray signals by delays that are individually controlled and provides delayed subarray signals which are summed to provide a beamformer signal.

30 Claims, 12 Drawing Sheets

| Phase value | adder bit 3 | adder bit 2 | adder bit 1 | Swch A | Swch B | Swch C | Swch D | Swch E | Swch F | Swch G | Swch H |
|---|---|---|---|---|---|---|---|---|---|---|---|
| 0 dgs | 0 | 0 | 0 | 0 | 1 | 0 | 1 | 1 | 1 | 0 | 0 |
| -45 dgs | 0 | 0 | 1 | 0 | 1 | 0 | 1 | 1 | 0 | 1 | 0 |
| -90 dgs | 0 | 1 | 0 | 1 | 0 | 0 | 1 | 0 | 0 | 1 | 1 |
| -135 dgs | 0 | 1 | 1 | 1 | 0 | 0 | 1 | 1 | 0 | 1 | 0 |
| -180 dgs | 1 | 0 | 0 | 1 | 0 | 1 | 0 | 1 | 1 | 0 | 0 |
| -225 dgs | 1 | 0 | 1 | 1 | 0 | 1 | 0 | 0 | 0 | 1 | 0 |
| -270 dgs | 1 | 1 | 0 | 0 | 1 | 1 | 0 | 1 | 0 | 1 | 1 |
| -315 dgs | 1 | 1 | 1 | 0 | 1 | 1 | 0 | 1 | 0 | 1 | 0 |

Fig. 7

BEAMFORMING METHODS AND APPARATUS FOR THREE-DIMENSIONAL ULTRASOUND IMAGING USING TWO-DIMENSIONAL TRANSDUCER ARRAY

FIELD OF THE INVENTION

This invention relates to medical ultrasound imaging and, more particularly, to beamforming techniques for three-dimensional ultrasound imaging using a two-dimensional transducer array.

BACKGROUND OF THE INVENTION

Medical ultrasound imaging systems typically use a one-dimensional phased array to form an image of a two-dimensional slice through a patient's body. This approach has limitations. First, the two-dimensional slice is always perpendicular to the face of the transducer, thereby limiting the choice of views. For example, a cardiologist sometimes wants to view heart valves in plane. This requires a double oblique imaging plane with respect to the face of the transducer. This plane can only be derived from three-dimensional data. Second, anatomy such as the left ventricle is inherently three-dimensional. To obtain an accurate volume measurement of the left ventricle, three-dimensional data must be acquired.

Current methods used to acquire three-dimensional data, such as may be obtained using Hewlett-Packard's Omni Plane transducers, use a one-dimensional array that is mechanically moved in a second dimension. This method may require several minutes to obtain a three-dimensional data set. Furthermore, the organs of interest may move during acquisition of the three-dimensional data set.

Phased array ultrasound transducers having multiple elements in the azimuth direction and a few elements in the elevation direction permit scanning in the azimuth direction and elevation focusing. See for example, U.S. Pat. No. 5,462,057 issued Oct. 31, 1995 to Hunt et al. These transducer configurations, often referred to as 1.5 dimensional arrays, do not permit beam steering in the elevation direction.

A system capable of acquiring real time three-dimensional data by electronically steering in two dimensions is described by T. Ota in "Accuracy of Left Ventricular Stroke Volume Measurement Using Real-Time, Three Dimensional Echocardiography Flow Probe in Vivo", 70th Scientific Session American Heart Association Meeting, Nov. 11, 1997. This system uses 512 active transducer elements. Signals from the transducer elements are passed through a cable having 512 coaxial conductors into a system with appropriate electronics. The image quality of the system is limited due to the small number of transducer elements used. Furthermore, since the cable between the transducer and the system has a significant diameter, it is unlikely that this technology can be extended to many more transducer elements without an unacceptably large cable or a cable with such small diameter conductors that significant signal loss will occur.

A two-dimensional phased array ultrasound imaging system wherein signal delays are distributed between a probe and a base station are described in U.S. Pat. No. 5,229,933 issued Jul. 20, 1993 to Larson, III et al.

A portable ultrasound imaging system wherein a handheld scan head enclosure houses an array of ultrasonic transducers, transmit circuitry and beamforming circuitry is disclosed in U.S. Pat. No. 5,590,658 issued Jan. 7, 1997 to Chiang et al. It is not considered feasible to incorporate all transmitting circuitry and beamforming circuitry for a three-dimensional phased array scanner into a handheld scan head of practical size.

An ultrasound beamformer which utilizes subarray processors to reduce the cost, power and size of digital beamformers is disclosed in U.S. Pat. No. 5,573,001 issued Nov. 12, 1996 to Petrofsky et al. Each subarray processor includes at least one phase shifter and a summer. Each phase shifter is responsive to at least one of the transducer signals to shift the transducer signal by a respective phase angle and to apply the phase shifted transducer signals to the summer. The summed subarray signals are applied to a beamformer processor. The disclosed beamformer is used for two-dimensional imaging.

A device for a three-dimensional focusing of an ultrasonic beam is disclosed in U.S. Pat. No. 5,027,820 issued Jul. 1, 1991 to Pesque. The device includes a cylindrical phased array.

None of the known prior art ultrasound imaging techniques have achieved high quality three-dimensional ultrasound imaging with transducer assemblies that are practical in size, cost and complexity.

SUMMARY OF THE INVENTION

According to a first aspect of the invention, a subarray receive beamformer is provided for use in an ultrasound imaging system. The ultrasound imaging system includes a two-dimensional array of transducer elements that define a plurality of subarrays. The subarray beamformer comprises receive circuitry responsive to transducer signals generated by receive elements of an associated subarray in response to received ultrasound energy for providing first and second subarray signals and a phase shift network for phase shifting and combining the first and second subarray signals to provide a phase shifted subarray signal. The first and second subarray signals each comprise a sum of weighted component signals derived from the transducer signals.

The receive circuitry of the subarray beamformer may comprise a phase control circuit for each of the receive elements in the associated subarray. Each phase control circuit may comprise means for providing a first component signal of the first subarray signal and a second component signal of the second subarray signal responsive to a transducer signal from a corresponding receive element and responsive to a phase shift value. The phase shift values may be representative of a desired steering angle for the subarray. The phase control circuit may comprise an amplifier circuit, first and second variable amplitude circuits and a control circuit. The amplifier circuit provides inverted and noninverted signals in response to the transducer signals. The first variable amplitude circuit attenuates the inverted or noninverted signal in response to first control signals and provides the first component signal of the first subarray signal. The second variable amplitude circuit attenuates the inverted or noninverted signal in response to second control signals and provides the second component signal of the second subarray signal. The control circuit supplies the first and second control signals to the first and second variable amplitude circuits, respectively, in response to the phase shift value.

According to another aspect of the invention, an ultrasound transducer assembly is provided for use in an ultrasound imaging system. The transducer assembly comprises a transducer handle, a transducer connector for connecting the transducer assembly to an electronics unit of the ultrasound imaging system and a transducer cable interconnecting the handle and the connector. The transducer handle includes a housing that contains a two-dimensional array of transducer elements that define a plurality of subarrays and a subarray processor associated with each of the subarrays. Each subarray processor provides first and second subarray signals in response to transducer signals generated by receive elements of the associated subarray in response to received ultrasound energy. The first subarray signal comprises a sum of first weighted component signals, and the second subarray signal comprises a sum of second weighted component signals. The first and second component signals are derived from the respective transducer signals. The connector includes a housing that contains a phase shift network associated with each of the subarrays for phase shifting and combining the first and second subarray signals to provide a phase shifted subarray signal.

According to a further aspect of the invention, an ultrasound imaging system is provided. The imaging system comprises a two-dimensional array of ultrasound transducer elements, a transmitter, a plurality of subarray processors and phase shift networks, a primary beamformer and an image generating circuit. The transducer elements define a plurality of subarrays. A subarray processor and a phase shift network are associated with each of the subarrays. The transmitter transmits ultrasound energy into a region of interest along a desired scan line in a three-dimensional space with transmit elements of the transducer. Each subarray processor comprises receive circuitry for providing first and second subarray signals in response to transducer signals generated by receive elements of the associated subarray in response to ultrasound energy received from the region of interest. The first subarray signal comprises a sum of first weighted component signals, and the second subarray signal comprises a sum of second weighted component signals. The first and second component signals are derived from the respective transducer signals. The phase shift network phase shifts and combines the first and second subarray signals to provide a phase shifted subarray signal. The primary beamformer comprises a delay circuit associated with each of the subarrays for delaying the phase shifted subarray signals by delays that are individually controlled and providing delayed subarray signals, and a summing circuit for summing the delayed subarray signals and providing a beamformer signal. The image generating circuit generates an image of the region of interest in response to the beamformer signal.

The ultrasound imaging system may include a transducer assembly and an electronics unit. The transducer assembly may comprise a transducer handle containing the array of transducer elements and the subarray processors, a transducer connector for connecting the transducer assembly to the electronics unit and a transducer cable interconnecting the transducer handle and the transducer connector. In a first configuration, the phase shift networks may be located in the transducer connector. In a second configuration, the phase shift networks may be located in the electronics unit. In a third configuration, the phase shift networks may be located in the transducer handle.

The subarray processors may each further comprise registers for holding an initial phase shift value and incremental x and y phase shift values. Each of the receive elements of the array may have an associated adder for determining an element phase shift value in response to the initial phase shift value and the incremental phase shift values. In one configuration, transmit circuitry associated with each of the subarrays is part of the subarray processor.

According to a further aspect of the invention, an ultrasound imaging system includes a two-dimensional array of ultrasound transducer elements that define a plurality of subarrays, a transmitter for transmitting ultrasound energy, a subarray processor associated with each of the subarrays, a primary beamformer and an image generating circuit as described above. Instead of using phase shift networks to phase shift the subarray signals generated by the subarray processors, the first and second subarray signals are provided to separate channels of the primary beamformer. The channels of the primary beamformer are programmed to have 90° of equivalent delay between them. Thus, the primary beamformer performs the function of the phase shift network.

BRIEF DESCRIPTION OF THE DRAWINGS

For a better understanding of the present invention, reference is made to the accompanying drawings, which are incorporated herein by reference and in which:

FIG. 7 is a table that illustrates the function of the switch control logic of FIG. 6;

DETAILED DESCRIPTION

Figure 1:
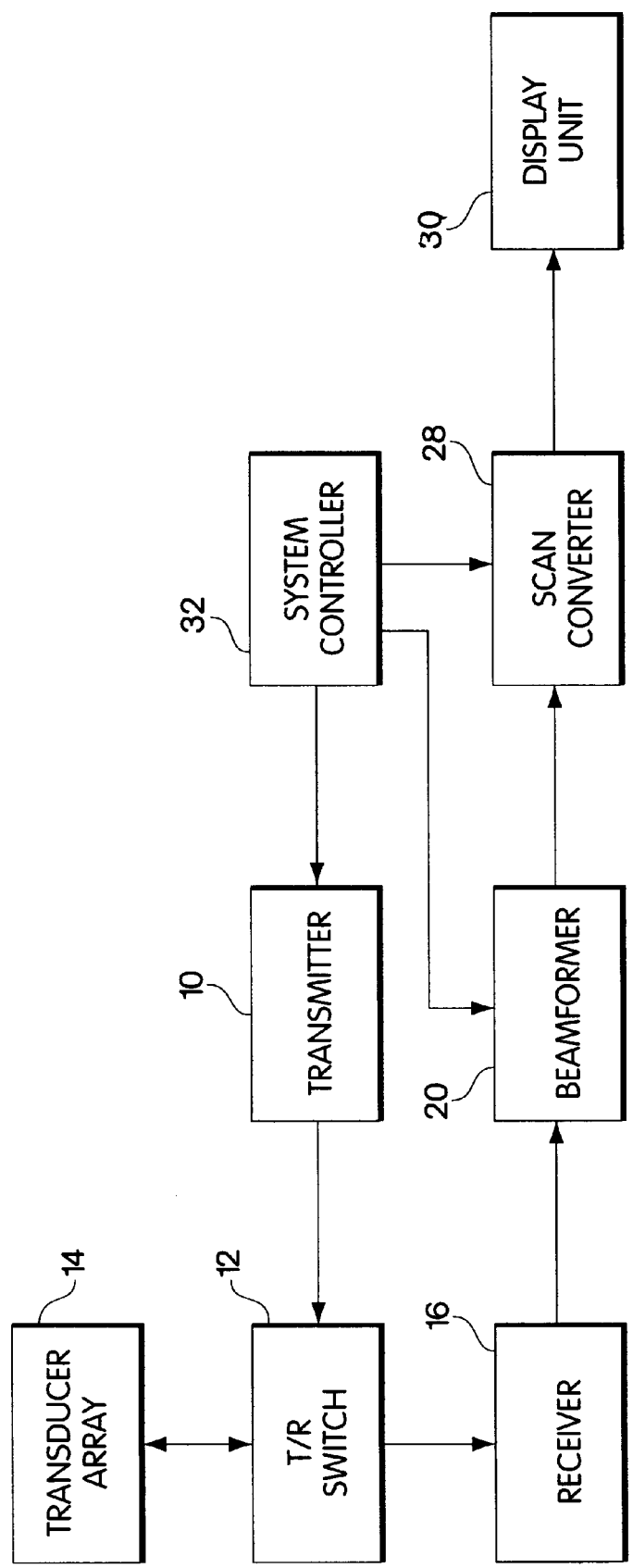
FIG. 1 is a block diagram of an ultrasound imaging system.

A simplified block diagram of an ultrasound imaging system is shown in FIG. 1. A transmitter 10 is coupled through a transmit/receive (T/R) switch 12 to a transducer array 14. The transducer array transmits ultrasound energy into a region being imaged and receives reflected ultrasound energy, or echoes, from various structures and organs within the patient's body. The transducer array 14 includes an array of transducer elements. As is known in the art, by appropriately delaying the pulses applied to each transducer element by transmitter 10, a focused ultrasound beam is transmitted along a desired scan line. The transducer array 14 is a two-dimensional array which permits steering of the transmitted and received ultrasound beams in both azimuth and elevation.

The transducer array 14 is coupled through T/R switch 12 to an ultrasound receiver 16. Ultrasound energy scattered from a given point within the patient's body is received by the transducer elements at different times. The transducer elements convert the received ultrasound energy to transducer signals which are amplified by receiver 16 and are supplied to a receive beamformer 20. The signals from each transducer element are individually delayed and then are summed by the beamformer 20 to provide a beamformer signal that represents the received ultrasound level along a desired scan line. As known in the art, the delays applied to the transducer signals may be varied during reception of ultrasound energy to effect dynamic focusing. The process is repeated for multiple scan lines to provide signals for generating an image of a region of interest in the patient's body. Typically, the scan pattern is a sector scan, wherein the scan lines originate at the center of the transducer array and are directed at different angles. Linear, curvilinear and other scan patterns may also be utilized.

The beamformer signal is applied to a scan converter 28 which converts sector scan signals generated by beamformer 20 to conventional raster display signals. The output of scan converter 28 is supplied to a video display unit 30, which displays an image of the region of interest in the patient's body. A system controller 32 provides overall control of the system. The system controller 32 performs timing and control functions and typically includes a microprocessor and associated memory.

The T/R switch 12 is used when elements of transducer array 14 are used for both transmitting and receiving. It will be understood that in this case a T/R switch element is required for each transducer element. In other embodiments, described below, different transducer elements may be used for transmitting and receiving. In that case, transmitter 10 is connected directly to the transmitting elements of transducer array 14, and receiver 16 is connected directly to receiving elements of transducer array 14.

In accordance with the invention, an ultrasound imaging system that utilizes a two-dimensional transducer array to generate three-dimensional images of a region of interest is provided. Speed is achieved by electronically steering transmit and receive beams in azimuth and elevation. Transducer array 14 has a large number of elements, such as for example 3,000 transducer elements, to achieve high image quality. The transducer in an ultrasound system is conventionally located in a handheld transducer head, or handle, connected by a flexible cable to an electronics unit that processes the transducer signals and generates an image of a region of interest. A cable having 3,000 conductors would be impractically large, bulky and inflexible. According to one feature of the invention, subarray processors may be incorporated into the transducer handle, thereby substantially reducing the number of conductors in the cable. According to another feature of the invention, phase shift networks may be incorporated into the transducer connector.

In one example, transducer array 14 includes 3,000 elements grouped into 120 subarrays, each including 5×5=25 elements. Approximately half of the transducer elements are used to transmit ultrasound energy, and the others are used to receive ultrasound energy. Separating transmit and receive elements eliminates the need for T/R switch 12, thereby reducing complexity and saving power. It will be understood that a T/R switch element would be required for each element of the transducer array. The transducer array 14 may have a sector scan geometry, a linear geometry, a curved linear geometry or any other suitable geometry.

Figure 2:
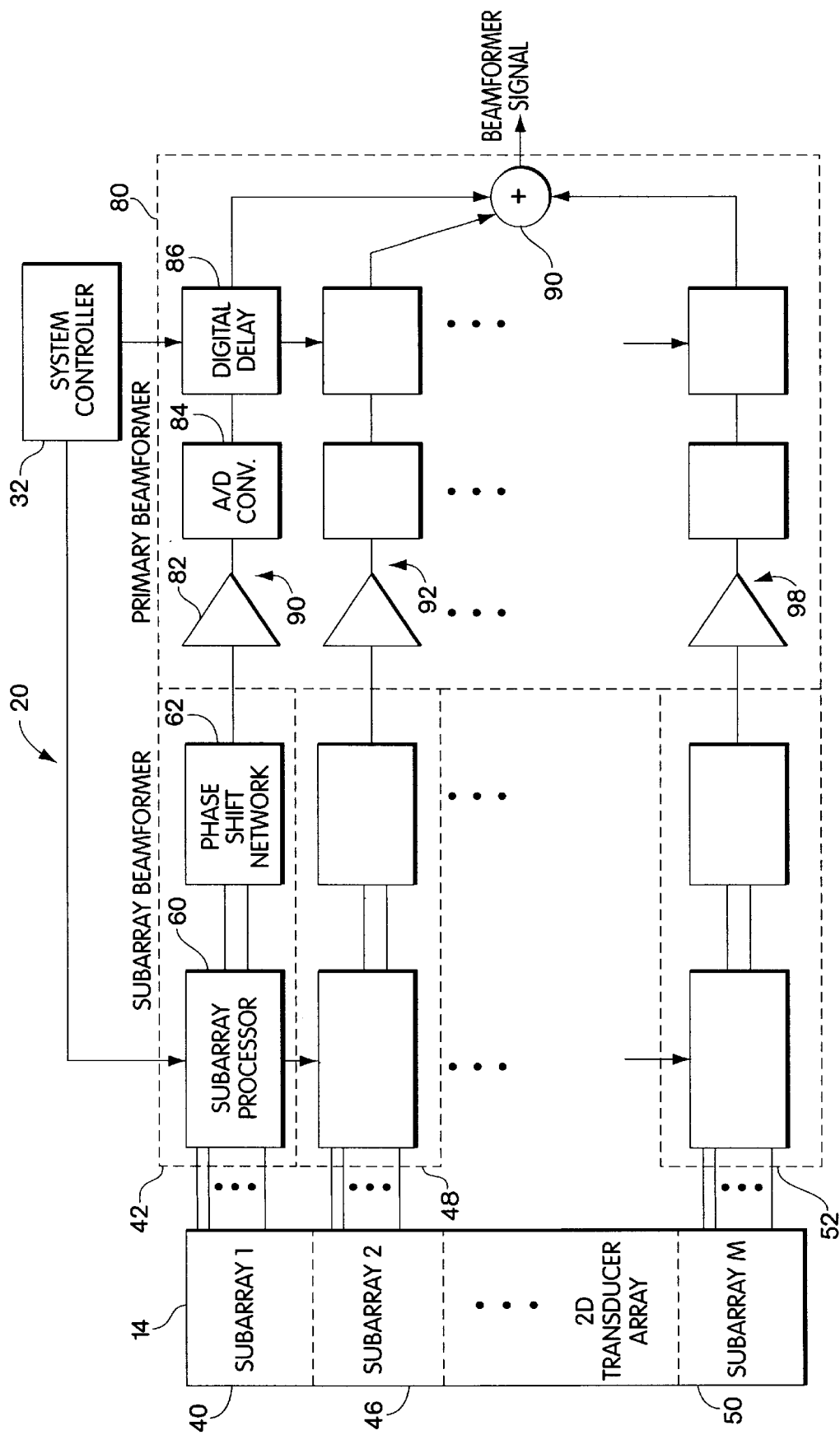
FIG. 2 is a block diagram of a beamformer including a primary beamformer and multiple subarray beamformers.

A block diagram of the beamformer architecture of the present invention is shown in FIG. 2. Each subarray of transducer array 14 is connected to a subarray beamformer. In particular, subarray 40 is connected to a subarray beamformer 42; subarray 46 is connected to a subarray beamformer 48; and subarray 50 is connected to a subarray beamformer 52. Each subarray beamformer includes a subarray processor 60 connected to the individual elements of the respective subarray and a phase shift network 62 connected to outputs of subarray processor 60. The phase shift network 62 in each subarray beamformer supplies a phased shifted subarray signal representative of received ultrasound energy along a desired scan line to a primary beamformer 80. As discussed below, the subarray beamformers are preferably located in the transducer assembly, so that each subarray provides a single phase shifted subarray signal to primary beamformer 80.

Primary beamformer 80 includes a beamformer channel corresponding to each subarray of transducer array 14. The outputs of subarray beamformers 42, 48, . . . 52 are provided to beamformer channels 90, 92, . . . 98, respectively, of primary beamformer 80. Each beamformer channel may include a variable gain TGC amplifier 82, an analog-to-digital converter 84 and a digital delay 86. The variable gain amplifier 82 controls gain as a function of received signal depth. The analog-to-digital converter 84 converts the analog output of amplifier 82 to digital format. The digital delay 86 delays the data samples to effect beam steering and dynamic focusing. The outputs of the beamformer channels are summed by a summing unit 90 to provide a beamformer signal that represents the received ultrasound energy along a desired scan line.

In the example described above, beamformer 20 includes 120 subarray beamformers, and primary beamformer 80 has 120 beamformer channels. The primary beamformer 80 may, for example, be a digital beamformer of the type used in the HP Sono 5500 ultrasound system, manufactured and sold by Hewlett-Packard Company. A time multiplexed digital ultrasound beamformer is disclosed in U.S. Pat. No. 5,469,851 issued Nov. 28, 1995 to Lipschutz.

System controller 32 supplies phase shift values to each of the subarray processors 60 for transmit beam steering and receive beam steering. The system controller 32 also supplies delay values to digital delay elements 86 for receive beam steering and dynamic focusing.

Figure 3:
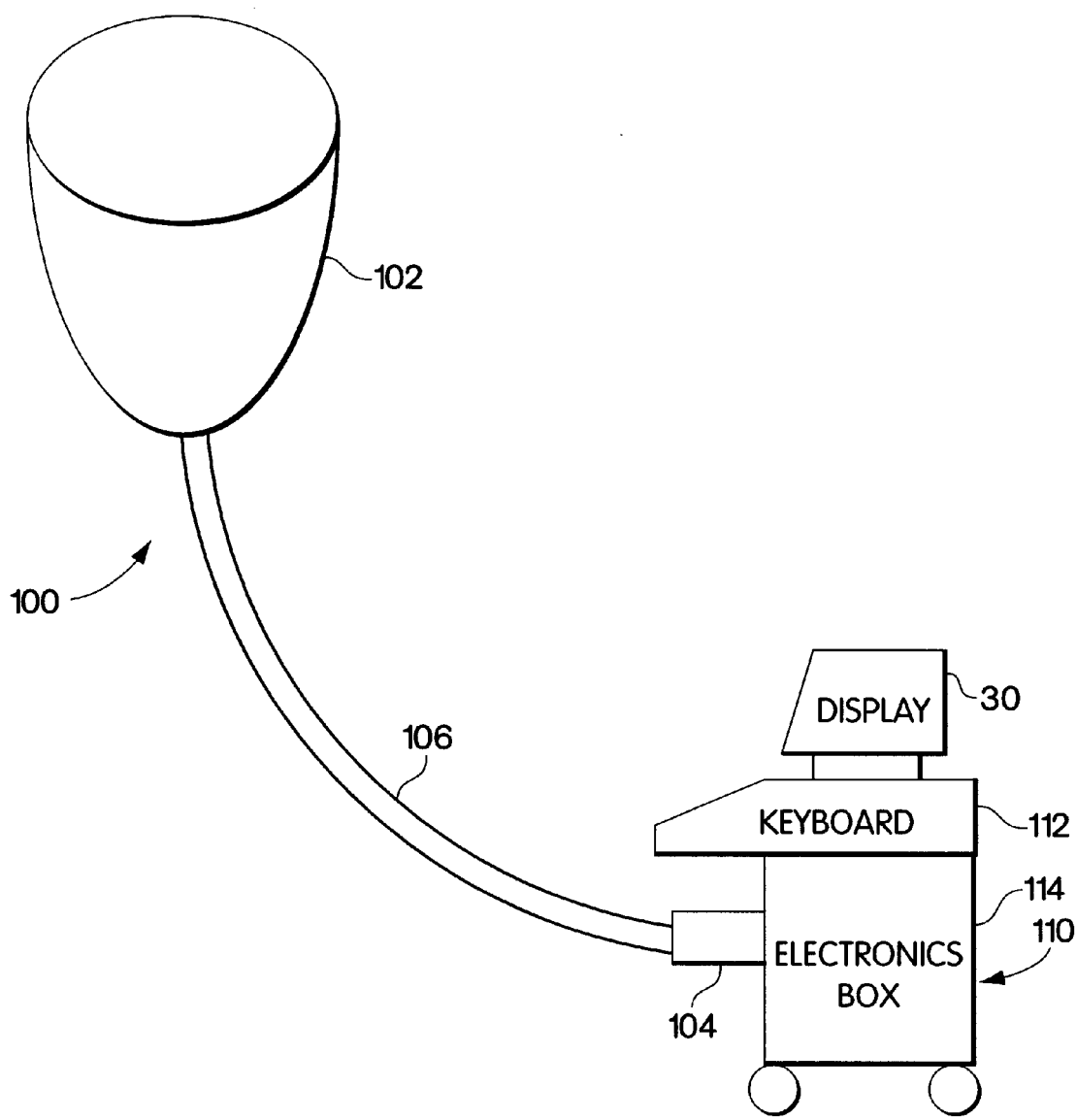
FIG. 3 is a pictorial view of an ultrasound imaging system.

A pictorial view of an ultrasound imaging system incorporating the present invention is shown in FIG. 3. A transducer assembly 100 (not shown to scale) includes a transducer handle, or head, 102, a transducer connector 104 and a cable 106 interconnecting handle 102 and connector 104. The transducer assembly 100 is attached by connector 104 to an electronics console 110, which may include display unit 30, a keyboard 112 and an electronics box 114. In a preferred embodiment of the invention, the transducer array 14 and subarray processors 60 are mounted within transducer handle 102, and phase shift networks 62 are mounted within transducer connector 104. It will be understood that different packaging configurations may be utilized within the scope of the present invention.

Figure 4:
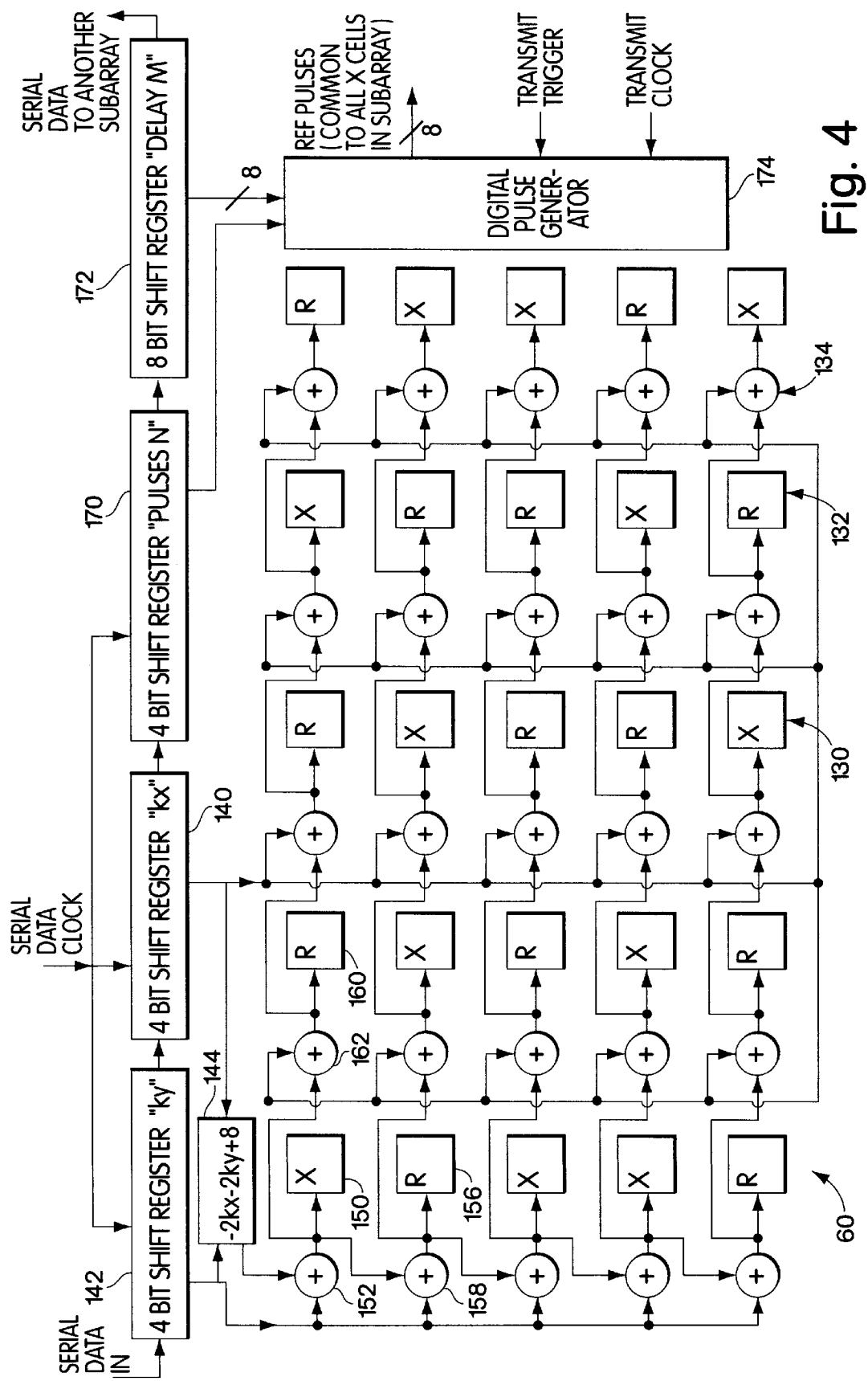
FIG. 4 is a block diagram of an example of a subarray processor in accordance with the invention.

A block diagram of an example of subarray processor 60 is shown in FIG. 4. In this example, each subarray includes a 5×5=25 transducer elements, with 12 transmit elements and 13 receive elements interspersed in a semi-random pattern. As shown in FIG. 4, each subarray processor 60 includes 12 transmit circuits 130 (marked with an X), 13 receive circuits 132 (marked with an R) and 25 adders 134. An adder 134 is associated with each of the transmit circuits 130 and with each of the receive circuits 132. One transmit circuit 130 is associated with each of the 12 transmit elements in the subarray, and one receive circuit 132 is associated with each of the 13 receive elements of the subarray. The subarray processor 60 further includes a shift register 140 for holding an x phase shift increment, a shift register 142 for holding a y phase shift increment and a register 144 for holding an initial phase shift value.

The initial phase shift value and the x and y phase shift increments may be used for steering the transmit and receive beams of each subarray. In particular, each transmit and receive circuit in subarray processor 60 is provided with a phase shift value that differs from the phase shift value of its nearest neighbor in the y direction by the y phase shift increment and differs from its nearest neighbor in the x direction by the x phase shift increment. The appropriate phase shift values for the transducer elements are derived from the initial phase shift value in the x and y phase shift increments by adders 134. The phase shift value for transmit circuit 150 at the left side of the first row and the top of the first column is determined by adder 152 from the initial phase shift value summed with the y phase shift increment. The remaining phase shift values in the first column are determined by adding the phase shift value from the element that is above the current element and the y phase shift increment. For example, the phase shift value for receive circuit 156 is determined by adder 158 as the sum of the output of adder 152 and the y phase shift increment from register 142. The remaining phase shift values in each row are determined by adding the phase shift value from the element that is to the left of the current element and the x phase shift increment. For example, the phase shift value for receive circuit 160 is determined by adder 162 as the sum of the output of adder 152 and the x phase shift increment from register 140. In this way, adders 134 determine 25 phase shift values from the initial phase shift value and the x and y phase shift increments.

The subarray processor 60 further includes a shift register 170 that holds a value representative of the number N of pulses to be transmitted for each transmit event, a shift register 172 that holds a delay value M representative of a delay between a trigger pulse and the first transmit pulse, and a digital pulse generator 174 for generating transmit pulse timing as described below.

Figure 5:
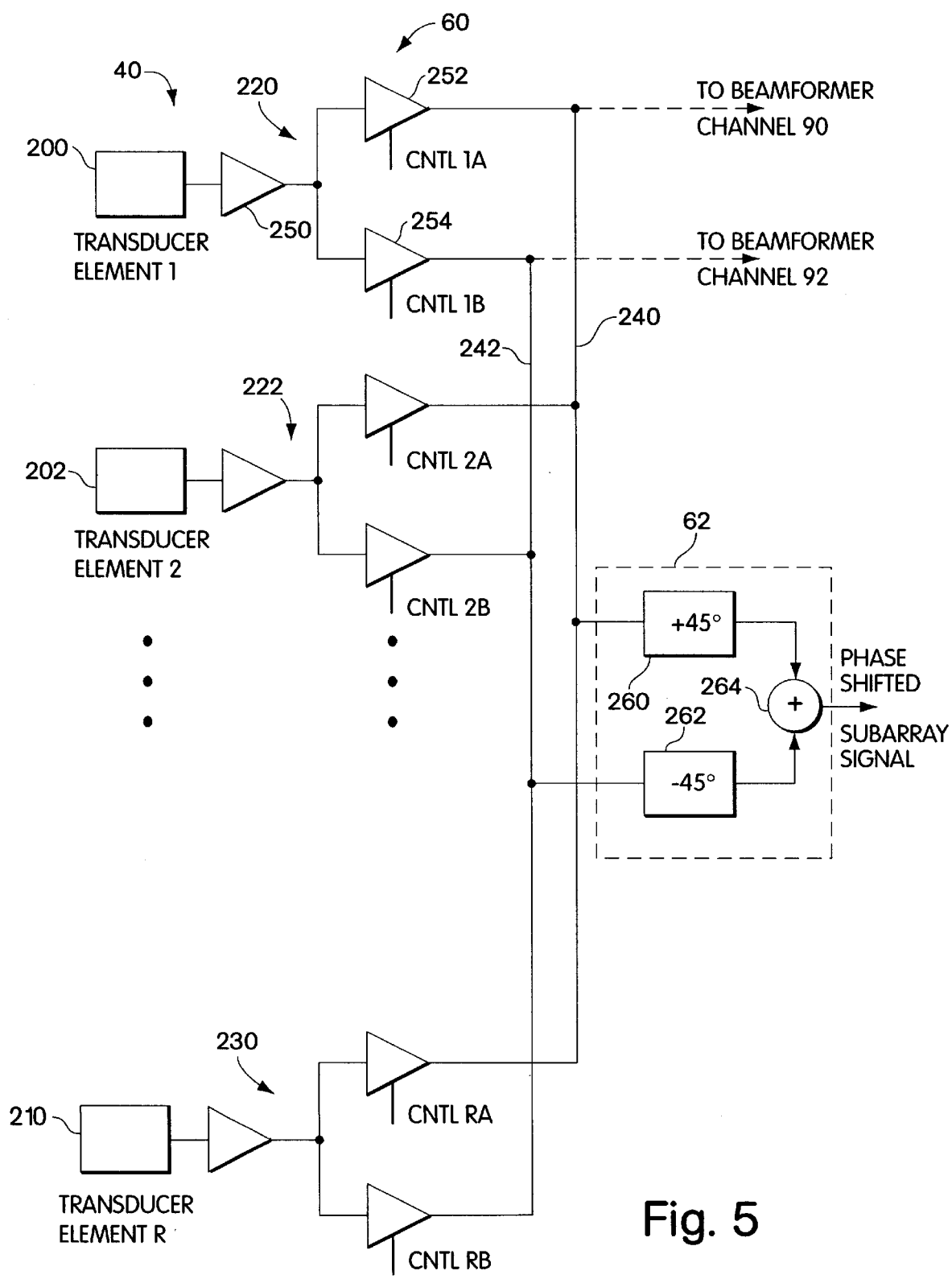
FIG. 5 is a functional block diagram of a subarray receive beamformer in accordance with the invention.

A simplified block diagram of a subarray receive beamformer in accordance with the invention is shown in FIG. 5. Subarray 40 of transducer array 14 (FIG. 2) includes receive transducer elements 200, 202, . . . 210. Each of the transducer elements 200, 202, . . . 210 receives ultrasound energy and converts the received ultrasound energy to a transducer signal. The transducer signals are provided to respective receive circuits in subarray processor 60. Transducer element 200 supplies a transducer signal to a receive circuit 220; transducer element 202 supplies a transducer signal to a receive circuit 222; and transducer element 210 supplies a transducer signal to a receive circuit 230. Each of the receive circuits comprises a phase control circuit that supplies a first component signal to a summing node 240 and a second component signal to a summing node 242. The summed first and second component signals at summing nodes 240 and 242 constitute first and second subarray signals, respectively. The phase control circuits control the phases of the respective transducer signals as described below.

Each of the receiving circuits 220, 222, . . . 230 includes a preamplifier 250 which receives the transducer signal from the respective transducer element and supplies an amplified signal to a first variable amplitude circuit 252 and to a second variable amplitude circuit 254. The output of first variable amplitude circuit 252 is connected to summing node 240, and the output of second variable amplitude circuit 254 is connected to summing node 252. The variable amplitude circuits 252 and 254 are supplied with control signals representative of a desired phase shift. The phase shifts collectively represent a desired steering angle of the receive beam for the subarray. The amplitudes of the component signals from each transducer element are controlled in accordance with the desired phase shift. Each variable amplitude circuit 252 supplies a first component signal of a first amplitude to summing node 240, and each variable amplitude circuit 254 supplies a second component signal of a second amplitude to summing node 242. The variable amplitude circuits 252 and 254 may be implemented as variable gain circuits or as variable attenuation circuits.

Summing node 240 is connected to a phase shifter 260 in phase shift network 62, and summing node 242 is connected to a phase shifter 262 in phase shift network 62. The phase shifters 260 and 262 preferably differ in phase shift by 90°. In the example of FIG. 5, phase shifter 260 provides a positive phase shift of 45°, and phase shifter 262 provides a negative phase shift of 45°. The outputs of phase shifters 260 and 262 are summed by a summing unit 264 to provide a phase shifted subarray signal. It will be understood that phase shifters 260 and 262 may have other phase shifts (e.g., 0° and 90°) which differ by 90°.

Different phase shifts of the transducer signals are obtained by varying the amplitudes of the component signals supplied to summing nodes 240 and 242. Assume for ease of understanding that the variable amplitude circuits 252 and 254 may control the component signal amplitudes between normalized values of 1 and 0. Thus, for example, when variable amplitude circuit 252 supplies an amplitude of 1 and variable amplitude circuit 254 supplies an amplitude of 0, the phase shift network 62 provides a phase shift of +45°. Similarly, when variable amplitude circuit 254 supplies an amplitude of 1 and variable amplitude circuit 252 supplies an amplitude of 0, the phase shift network 62 provides a phase shift of −45°. Other phase shift values may be obtained by appropriate adjustment of the relative amplitudes supplied by variable amplitude circuits 252 and 254. When inverted and noninverted transducer signals are supplied to variable amplitude circuits 252 and 254, phase shifts between 0° and 360° may be obtained, as described below.

Because the subarray receive beamformer of FIG. 5 is linear, the output of phase shift network 62 is the sum of the individually phase-shifted transducer signals. Since the phase shifts correspond to a desired steering angle, the output of phase shift network 62 is a beamformed signal representative of ultrasound energy received by the subarray at the desired steering angle.

Figure 6:
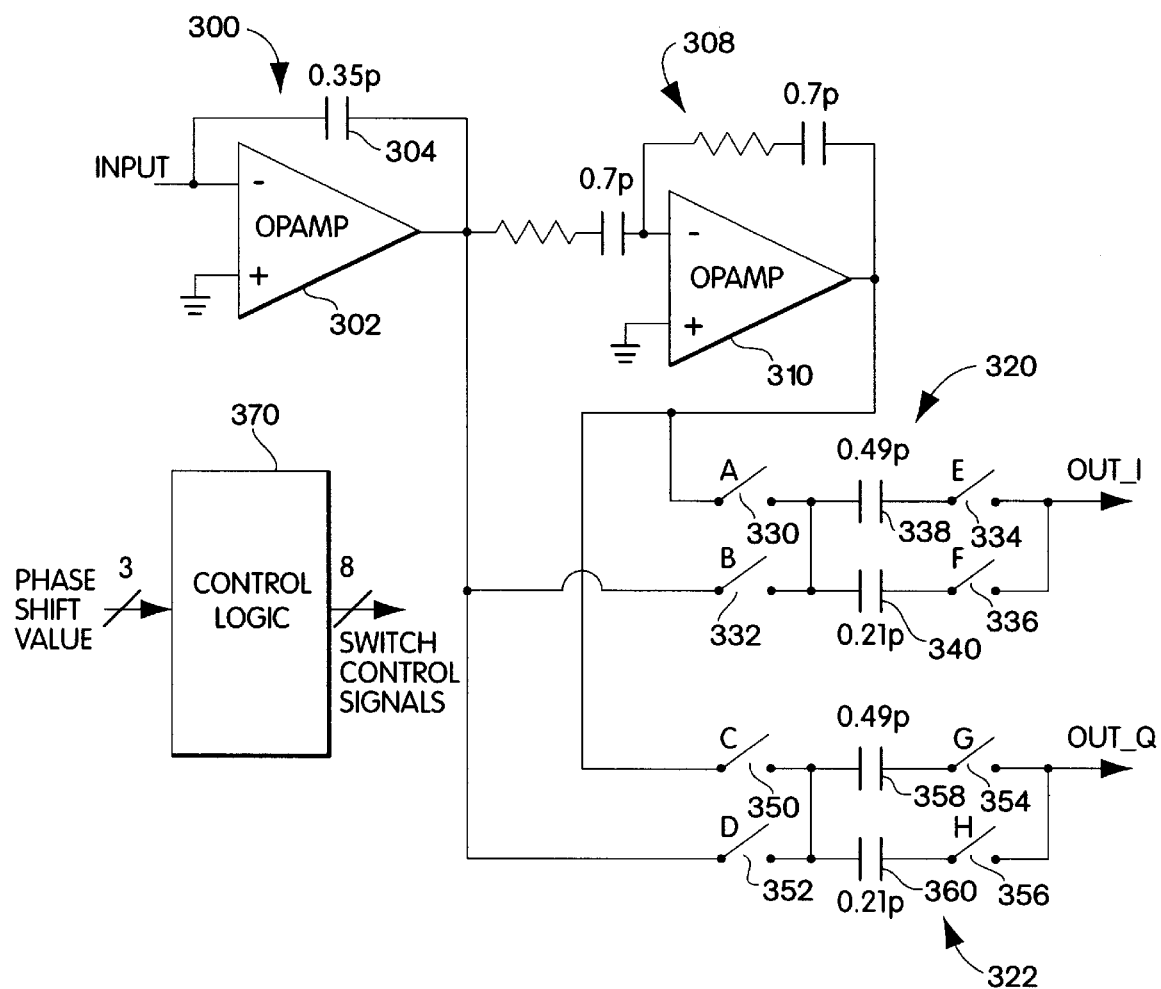
FIG. 6 is a block diagram of a receive circuit in the subarray processor of FIG. 2.

An example of an implementation of the receive circuit of the subarray processor of FIGS. 4 and 5 is shown in FIG. 6. The transducer signal is coupled to the input of a preamplifier 300 including an operational amplifier 302 and a feedback capacitor 304. The output of preamplifier 300 is connected to an input of an inverting amplifier circuit 308, including an operational amplifier 310 and input and feedback components which provide unity gain. Thus, amplifiers 300 and 308 produce equal amplitude, opposite phase (180° phase shift) representations of the transducer signal. The outputs of amplifiers 300 and 308, referred to as noninverted and inverted signals, respectively, are coupled to inputs of a first variable amplitude circuit 320 and to inputs of a second variable amplitude circuit 322.

The variable amplitude circuits 320 and 322 correspond to variable amplitude circuits 252 and 254, respectively, shown in FIG. 5. Variable amplitude circuit 320 includes electronically controlled switches 330, 332, 334 and 336, and capacitors 338 and 340. Switch 330 selectively couples the inverted signal to the first terminals of capacitors 338 and 340. Switch 332 selectively couples the noninverted signal to the first terminals of capacitors 338 and 340. Switch 334 selectively couples the second terminal of capacitor 338 to the output, and switch 336 selectively couples the second terminal of capacitor 340 to the output. Variable amplitude circuit 322 includes electronically controlled switches 350, 352, 354 and 356, and capacitors 358 and 360. Switch 350 selectively couples the inverted signal to the first terminals of capacitors 358 and 360, and switch 352 selectively couples the noninverted signal to the first terminals of capacitors 358 and 360. Switch 354 selectively couples the second terminal of capacitor 358 to the output, and switch 356 selectively couples the second terminal of capacitor 360 to the output.

Capacitors are used as attenuation elements because they do not contribute to thermal noise and are more linear than available resistors. Switches 330, 332, 334, 336, 350, 352, 354 and 356 may each be implemented as a p-type FET and an n-type FET connected in parallel. The sizes of the FET's are selected to place the RC pole beyond 5 MHz.

The receive circuit further includes control logic 370 which supplies control signals to switches 330, 332, 334, 336, 350, 352, 354 and 356. The control logic 370 receives inputs representative of the desired phase shift value from the respective adder in the subarray processor. Thus, for example, with reference to FIG. 4, the control logic in receive circuit 156 receives a phase shift value from adder 158. The control logic 370 implements the logic shown in the table of FIG. 7 to provide phase shifts of 0° to 315°0 in 45° increments. It will be understood that smaller phase shift increments may be obtained by increasing the number of switches and capacitors in the variable amplitude circuits and by increasing the number of bits used to specify the phase shift value. Amplifiers 300 and 308, variable amplitude circuits 320 and 322 and control logic 370 constitute a phase control circuit for controlling the phase of the transducer signal.

Figure 8:
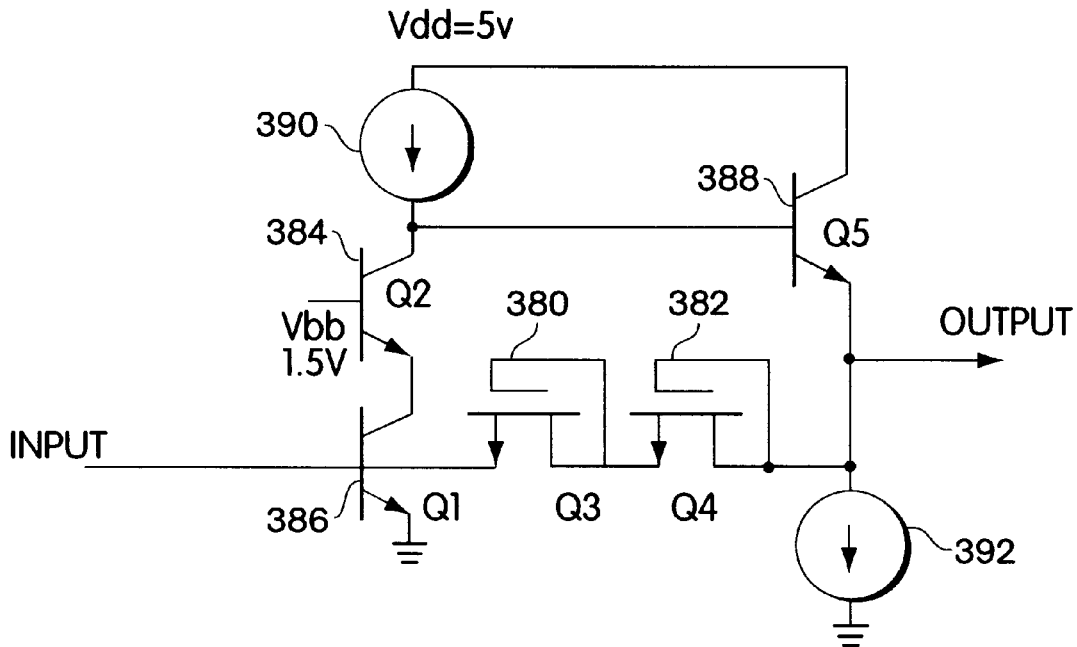
FIG. 8 is a schematic diagram of an example a suitable preamplifier for use in the receive circuit of FIG. 6.

An example of a suitable amplifier circuit for implementing amplifiers 300 and 310 is shown in FIG. 8. Transistors 380 and 382 act as diodes in series with a high resistance that clamps the output bias voltage at two FET thresholds plus a 0.7 volt Vbe drop. Cascode transistor 384 reduces the Miller effect of transistor 386. Transistor 388 acts as a low impedance output driver. Current sources 390 and 392 are formed by FET current mirrors that copy the current from an external reference current.

The reference current can be controlled to adjust the tradeoff between dynamic range and power dissipation. For modes such as CW Doppler that require a high dynamic range, the reference current can be set to a high value. Modes requiring less dynamic range, such as B-mode imaging, can use a lower value reference current. Furthermore, in B-mode, color flow, angio and pulse Doppler modes, the reference current can be swept dynamically as a function of receive depth, with high currents used to handle the large near field signals and low currents used to handle the small far field signals. The purpose of varying the reference current is to lower the circuit power dissipation.

Figure 9:
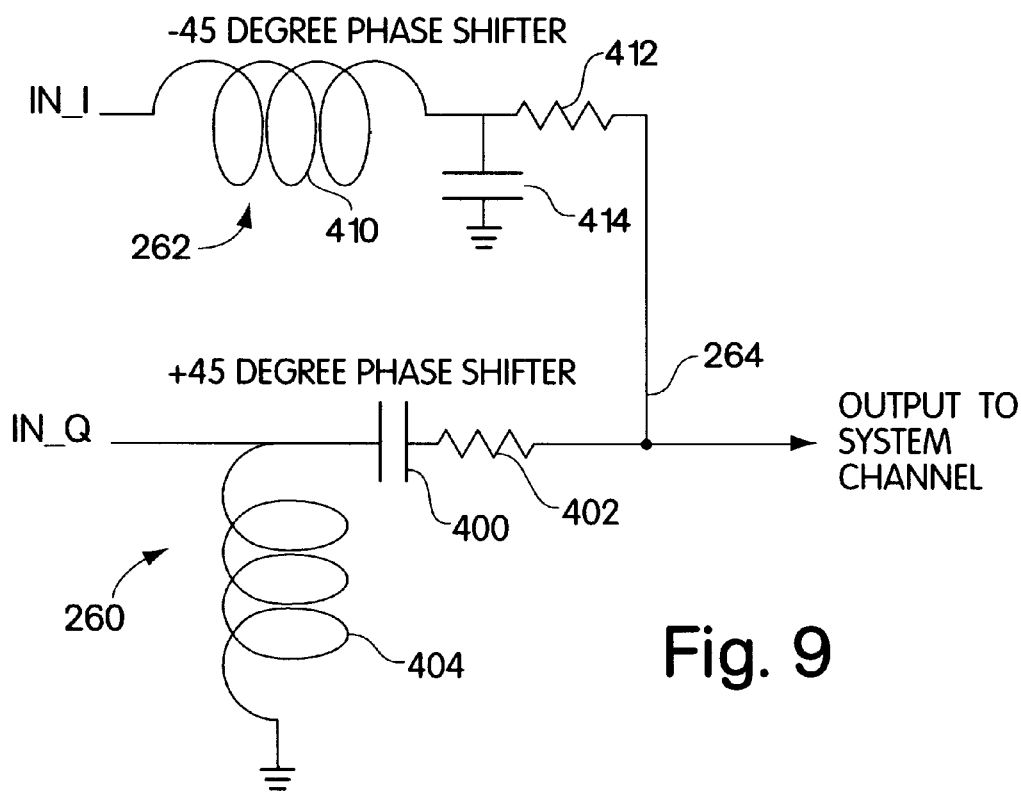
FIG. 9 is a schematic diagram of an example of a suitable phase shift network.

An example of an implementation of the phase shift network 62 is shown in FIG. 9. The +45° phase shifter 260 includes a capacitor 400 and a resistor 402 connected in series between the input and summing node 264, and a shunt inductor 404. The −45° phase shifter 262 includes an inductor 410 and a resistor 412 connected in series between the input and summing node 264, and a shunt capacitor 414. It will be understood that the values of the components depend on the operating frequency of the ultrasound transducer. As indicated above, the phase shift network may advantageously be located in the transducer connector 104 (FIG. 3). In other configurations the phase shift network may be located in electronics box 114 or in transducer handle 102.

As discussed above, the ultrasound imaging system may include 120 subarrays and 120 subarray processors which provide transmit and receive signals to and from the transducer elements. Signals from the receive circuits of each subarray are individually phase shifted and summed and supplied to one of 120 beamformer channels in primary beamformer 80 (FIG. 2). The phase shift networks within each subarray beamformer steer the subarray to receive along a desired scan line at a desired steering angle. The digital delays provided by the primary beamformer 80 synchronize the signals from the different subarrays. The digital delays applied by primary beamformer 80 may be selected to perform beam steering by defining delays between subarrays, to perform dynamic focusing and/or to perform parallel processing. The phase shifts applied to each transducer element by each subarray processor may steer the receive beam of the respective subarray. The digital delay can be changed dynamically with time as ultrasound energy is received, so as to provide dynamic focusing. Static focusing can be obtained by steering each subarray at a slightly different angle. This may be thought of as a piecewise linear approximation to the focus delay equation.

The phase shift values supplied to each subarray processor are described above as controlling the steering angle of the subarray. In general, the phase shift values are not limited to controlling the steering angle and may be used to provide any desired phase profile for the associated subarray. For example, it may be useful to individually focus one or more subarrays. Furthermore, the subarray processor is not limited to a configuration that processes an initial phase shift value and x and y phase shift increments as described above. In general, individual phase shift values may be provided for each of the transducer elements of the subarray.

Preferably the phase shifts provided by each subarray processor are static in the sense that their phase shift values are only updated once for each transmit event, for example, just before each transmit event. This allows simple, high density, low power CMOS switches to be used in the subarray processors, since their switching transients occur before any signals are received.

Referring again to FIG. 4, the adders 134 are used to calculate the phase shift values needed by each transmit and receive circuit. Since the phase shift values of each subarray are used only for steering the transmit and receive beams of the subarray, the phase shift for each transmit and receive circuit is a simple x or y phase shift increment from the phase shift needed by a neighboring circuit. The fixed phase shift increments kx and ky are provided by shift registers 140 and 142, respectively. The initial phase shift value in register 144 ensures that the center circuit of the subarray has a phase shift value centered within its range. Only the three most significant adder bits are used by each transmit and receive circuit. The adders 134 are preferably asynchronous with no lookahead carry circuitry in order to save power and circuit area.

Figure 10:
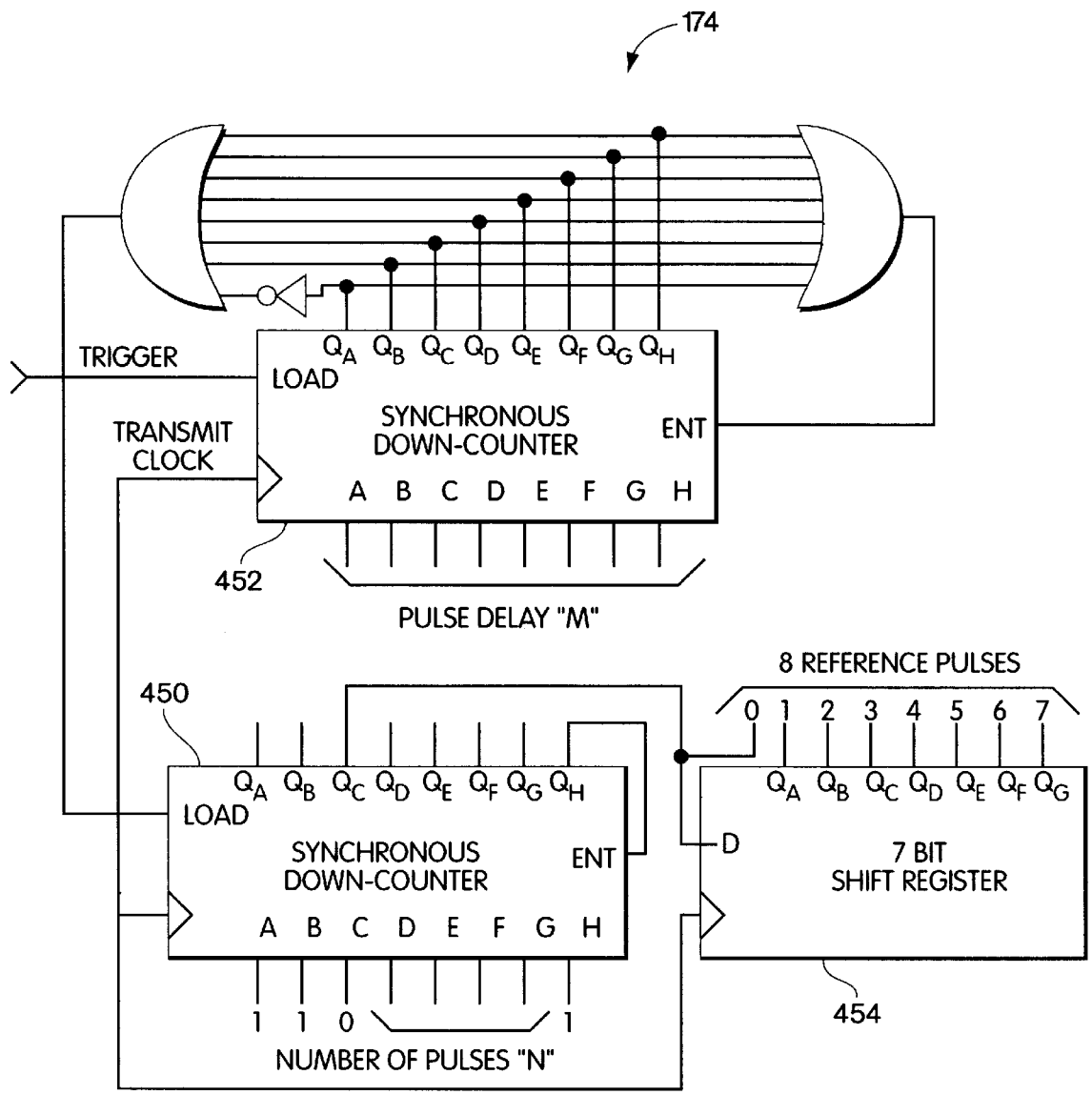
FIG. 10 is a block diagram of an example of the digital pulse generator shown in FIG. 4.
Figure 11:
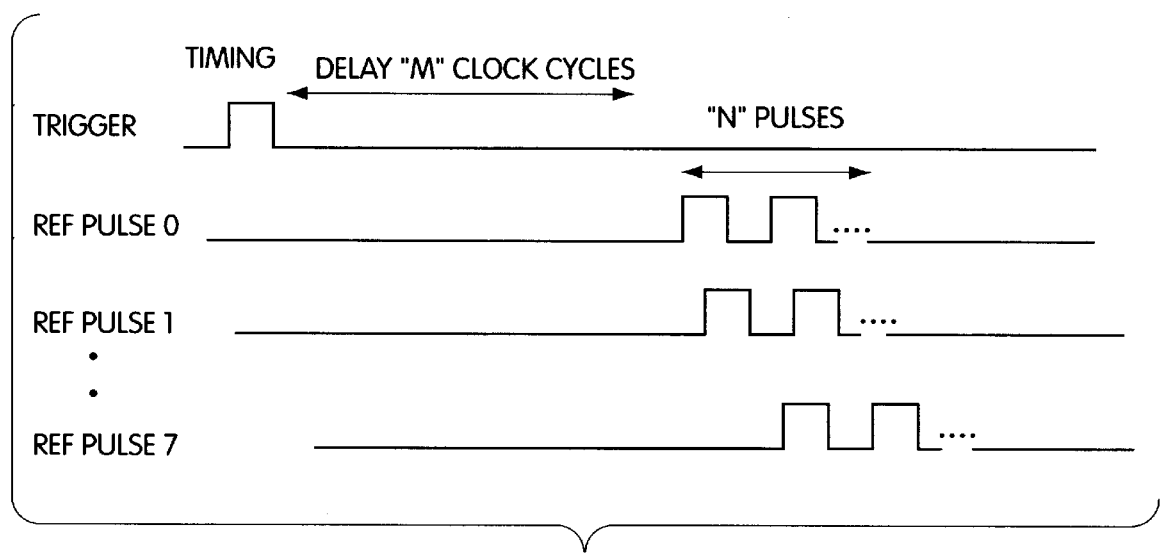
FIG. 11 is a timing diagram showing the reference pulses generated by the digital pulse generator of FIG. 8.
Figure 12:
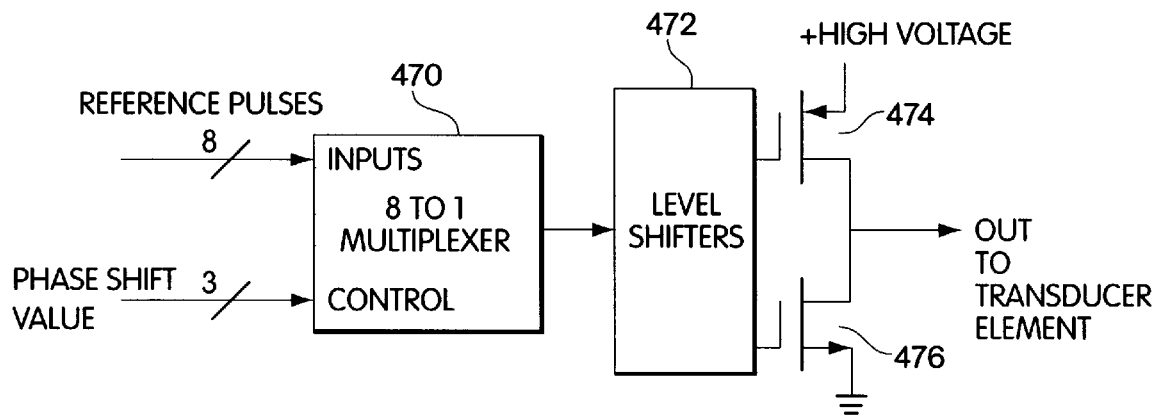
FIG. 12 is a block diagram of a transmit circuit in the subarray processor of FIG. 4.

The subarray processor circuitry associated with transmitting includes shift registers 170 and 172, digital pulse generator 174 and the individual transmit circuits associated with each transmit element of the transducer subarray. A block diagram of an example of a suitable digital pulse generator is shown in FIG. 10. A timing diagram illustrating the operation of the digital pulse generator is shown in FIG. 11. A block diagram of an example of a suitable transmit circuit is shown in FIG. 12. As shown in FIG. 11, the digital pulse generator 174 generates eight reference transmit pulses of N cycles long and delayed from a transmit trigger pulse by M transmit clock cycles plus eight different additional delays. These reference transmit pulses are sent to all the transmit circuits. As shown in FIG. 8, a synchronous counter 450 counts clock cycles for the number N of transmit pulses, and a synchronous counter 452 determines the pulse delay M. A shift register 454 provides the seven additional delay values required to produce the eight reference transmit pulses as shown in FIG. 11.

The pulse delay M relative to the transmit trigger varies from subarray to subarray depending on the steering angle of the transmit beam. The number of transmit pulses N depends on the transmit mode. In B-mode imaging, for example, a single pulse may be transmitted for each transmit event, whereas in Doppler imaging, more than one pulse may be transmitted for each transmit event.

As shown in FIG. 12, each transmit circuit may include a multiplexer 470 which receives the eight reference transmit pulses from the digital delay generator 174. One of the reference pulses is selected by multiplexer 470 based on a phase shift value received from the respective adder. For example, with reference to FIG. 4, transmit circuit 150 selects a reference pulse based on the phase shift value received from adder 152. The selected reference pulse is supplied through level shifters 472 to transmit driver transistors 474 and 476 for driving the respective transmit element of the transducer array.

An alternate embodiment of the beamformer of the present invention is described with reference to FIGS. 2 and 5. In this embodiment, the phase shift network 62 is not utilized. Instead, the first and second subarray signals output by each receive circuit are connected to different beamformer channels of primary beamformer 80. In particular, summing node 240 of subarray processor 60 may be connected to beamformer channel 90, and summing node 242 may be connected to beamformer channel 92, as indicated by dashed lines in FIG. 5. Similarly, the output signals of other subarray processors are connected to respective pairs of beamformer channels in primary beamformer 80. The beamformer channels 90 and 92 are programmed to have 90° of equivalent delay between them. This embodiment has the advantage of eliminating the phase shift networks 62, but has the disadvantage that the primary beamformer 80 is required to have twice as many beamformer channels for a given number of subarray processors.

The ultrasound imaging system of the present invention may perform parallel processing wherein two or more receive beams are processed simultaneously. The subarray beamformers provide subarray signals to the primary beamformers, and the primary beamformer processes two or more receive beams simultaneously, as described for example in the aforementioned U.S. Pat. No. 5,469,851. Using the two-dimensional transducer array and the subarray beamformers, the system can parallel process receive beams in azimuth and elevation simultaneously. As stated in U.S. Pat. No. 5,469,851, the parallel receive beams are within the beam pattern of the transmitted ultrasound energy.

An example of an implementation of an ultrasound imaging system in accordance with the invention is now described. The transducer array 14 may be a 3.5 MHz circular array having a 60 element diameter with 3,000 elements grouped into 120 subarrays of 25 elements each. In each subarray, 12 elements are used for transmit and 13 elements are used for receive. The transmit and receive elements are interspersed in a semi-random pattern. The transducer elements are spaced on a 210 micrometer grid. The transducer handle 102 (FIG. 3) includes transducer array 14 and 120 subarray processors. The subarray processors are packaged in 30 integrated circuits, with 4 subarray processors per chip. The transducer cable 106 includes 240 signal wires, 3 power supply wires, 4 clock lines, 15 serial digital data lines, 1 digital control line and 1 analog reference current. The transducer connector 104 contains 120 phase shift networks 62 as shown in FIG. 5 and described above. The electronics box 114 contains a digital beamformer as described in detail above.

Referring again to FIG. 4, data from one of the serial data lines loads data into the shift registers 140, 142, 170 and 172. One serial data line serves 2 integrated circuits, including 8 subarray processors. A 160 cycle 20 megahertz clock burst (serial data clock) transfers the data in 8 microseconds. After the data is clocked in and after all the asynchronous adders settle (approximately 1 microsecond), a transmit trigger pulse is provided, resulting in transmit energy being sent to the transducer array.

Figure 13:
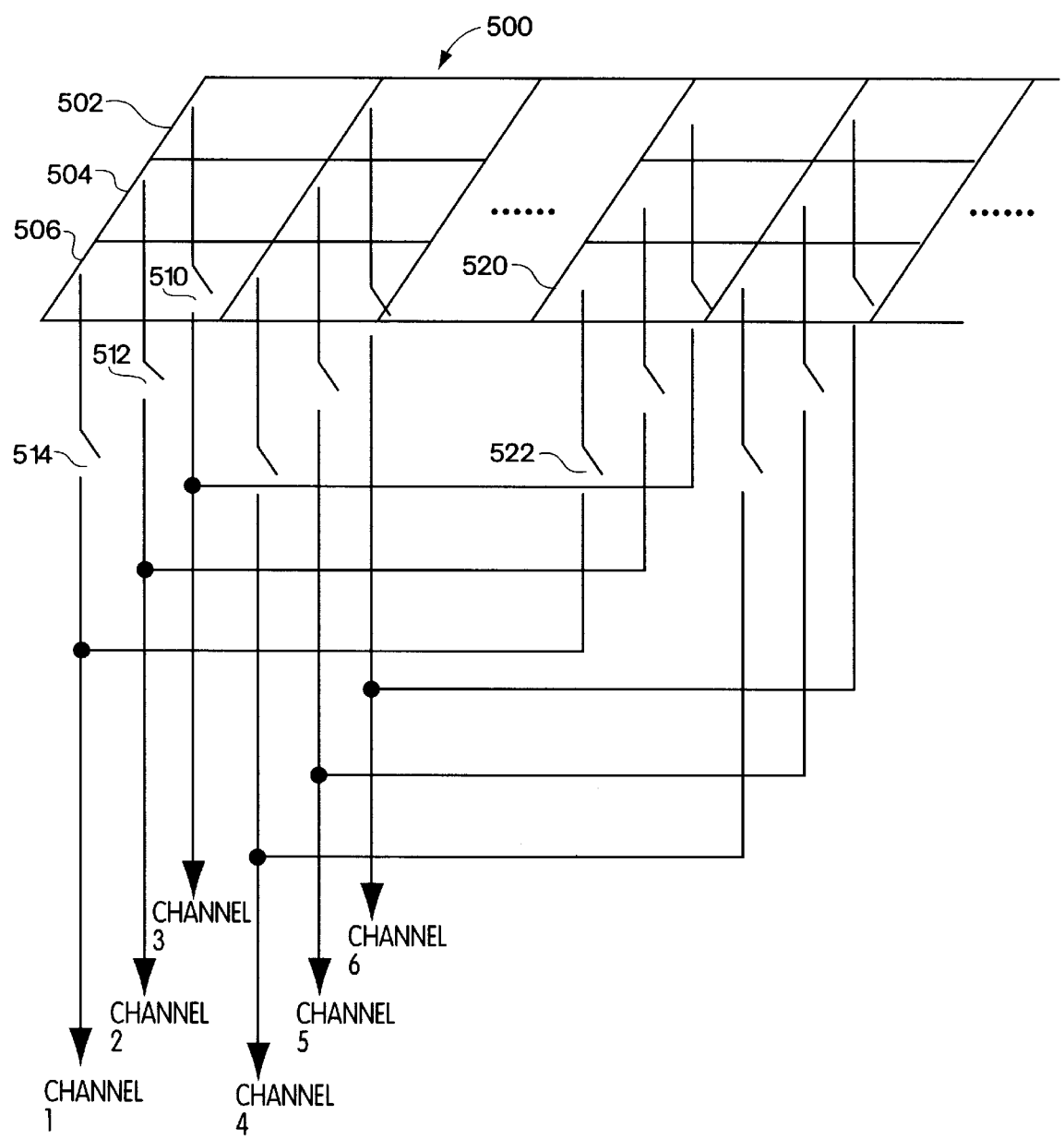
FIG. 13 is a schematic representation of a transducer array that is subdivided into subarrays and multiple subarray processors are connected to each system channel.

The discussions above have been based primarily on sector scan phased arrays. However, the subarray processing techniques described above can be used for other transducer geometries, such as linear and curved linear arrays. A further embodiment of the invention, wherein a linear array 500 divided into subarrays 502, 504, 506, etc., is shown in FIG. 13. Each subarray is connected to a subarray processor as described in detail above. Each system channel is selectively connected to more than one subarray processor through multiplexer switches 510, 512, 514, etc. Thus, for example, subarray 506 may be connected to channel 1 by closing switch 514, and subarray 520 may be connected to channel 1 by closing switch 522. The multiplexer switches permit an active aperture to be electronically moved across the array to provide a linear scan format along the length of the array. Sector, linear or combined format can be used in the elevation direction. The multiplexer switches may be integrated into the subarray processor integrated circuit. The power to subarray processors that are not selected may be turned off to save power.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A subarray receive beamformer for use in an ultrasound imaging system including a two-dimensional array of ultrasound transducer elements that define a plurality of subarrays, said subarray beamformer comprising:

receive circuitry, responsive to transducer signals generated by receive elements of an associated subarray in response to received ultrasound energy, wherein the receive elements of the associated subarray are distributed in at least two dimensions on said two-dimensional array, said receive circuitry providing first and second subarray signals, said first and second subarray signals each comprising a sum of weighted component signals derived from said transducer signals; and a phase shift network for phase shifting and combining said first and second subarray signals to provide a phase shifted subarray signal.

2. A subarray receive beamformer as defined in claim 1 wherein said receive circuitry comprises a phase control circuit for each of the receive elements in the associated subarray, each phase control circuit comprising means, responsive to a transducer signal from a corresponding receive element and responsive to a phase shift value, for providing a first component signal of said first subarray signal and a second component signal of said second subarray signal.

3. A subarray receive beamformer as defined in claim 2 wherein said phase control circuit comprises:

an amplifier circuit responsive to said transducer signals for providing inverted and noninverted signals;

a first variable amplitude circuit responsive to first control signals for attenuating said inverted or noninverted signal and providing said first component signal of said first subarray signal;

a second variable amplitude circuit responsive to second control signals for attenuating said inverted or noninverted signal and providing said second component signal of said second subarray signal; and a control circuit for supplying said first and second control signals to said first and second variable amplitude circuits, respectively, in response to said phase shift value.

4. A subarray receive beamformer as defined in claim 1 wherein said phase shift network comprises a first phase shifter for phase shifting said first subarray signal to provide a first phase shifted signal, a second phase shifter for phase shifting said second subarray signal to provide a second phase shifted signal and a summer for summing said first and second phase shifted signals to provide said phased shifted subarray signal.

5. An ultrasound transducer assembly for use in an ultrasound imaging system, comprising:

a transducer handle containing a two-dimensional array of ultrasound transducer elements that define a plurality of subarrays, and a subarray processor associated with each of said subarrays, each subarray processor comprising receive circuitry, responsive to transducer signals generated by receive elements of the associated subarray in response to received ultrasound energy, wherein the receive elements of the associated subarray are distributed in at least two dimensions on said two-dimensional array, said receive circuitry providing first and second subarray signals, said first subarray signal comprising a sum of first weighted component signals and said second subarray signal comprising a sum of second weighted component signals, said first and second component signals being derived from the respective transducer signals;

a transducer connector for connecting the transducer assembly to an electronics unit of the ultrasound imaging system, said connector including a housing containing a phase shift network associated with each of said subarrays for phase shifting and combining said first and second subarray signals to provide a phase shifted subarray signal; and a transducer cable interconnecting said handle and said connector.

6. An ultrasound transducer assembly as defined in claim 5 wherein the receive circuitry of each subarray processor comprises a phase control circuit for each of the receive elements in the associated subarray, each phase control circuit comprising means, responsive to a transducer signal from a corresponding receive element and responsive to a phase shift value, for providing a first component signal of said first subarray signal and a second component signal of said second subarray signal.

7. An ultrasound transducer assembly as defined in claim 6 wherein each phase control circuit comprises:

an amplifier circuit responsive to said transducer signal for providing inverted and noninverted signals;

a first variable amplitude circuit responsive to first control signals for attenuating said inverted or noninverted signal and providing said first component signal of said first subarray signal;

a second variable amplitude circuit responsive to second control signals for attenuating said inverted or noninverted signal and providing said second component signal of said second subarray signal; and a control circuit for supplying said first and second control signals to said first and second variable amplitude circuits, respectively, in response to said phase shift value.

8. An ultrasound transducer assembly as defined in claim 5 wherein said phase shift network comprises a first phase shifter for phase shifting said first subarray signal to provide a first phase shifted signal, a second phase shifter for phase shifting said second subarray signal to provide a second phase shifted signal and a summer for summing said first and second phase shifted signals to provide said phase shifted subarray signal.

9. An ultrasound imaging system comprising:

a two-dimensional array of ultrasound transducer elements that define a plurality of subarrays;

a transmitter for transmitting ultrasound energy into a region of interest along a desired scan line in a three-dimensional space with transmit elements of the array;

a subarray processor associated with each of said subarrays, each subarray processor comprising receive circuitry, responsive to transducer signals generated by receive elements of the associated subarray in response to ultrasound energy received from said region of interest, wherein the receive elements of the associated subarray are distributed in at least two dimensions on said two-dimensional array, said receive circuitry providing first and second subarray signals, said first subarray signal comprising a sum of first weighted component signals and said second subarray signal comprising a sum of second weighted component signals, said first and second component signals being derived from the respective transducer signals;

a phase shift network associated with each of said subarrays for phase shifting and combining said first and second subarray signals to provide a phase shifted subarray signal;

a primary beamformer comprising a delay circuit associated with each of said subarrays for delaying said phase shifted subarray signals by delays that are individually controlled and providing delayed subarray signals, and a summing circuit for summing said delayed subarray signals and providing a beamformer signal; and an image generating circuit responsive to said beamformer signal for generating an image of the region of interest.

10. An ultrasound imaging system as defined in claim 9 wherein the receive circuitry of each subarray processor comprises a phase control circuit for each of the receive elements in the associated subarray, each phase control circuit comprising means, responsive to a transducer signal from a corresponding receive element and responsive to a phase shift value, for providing a first component signal of said first subarray signal and a second component signal of said second subarray signal.

11. An ultrasound imaging system as defined in claim 10 wherein each phase control circuit comprises:
    an amplifier circuit responsive to said transducer signal for providing inverted and noninverted signals;
    a first variable amplitude circuit responsive to first control signals for attenuating said inverted or noninverted signal and providing said first component signal of said first subarray signal;
    a second variable amplitude circuit responsive to second control signals for attenuating said inverted or noninverted signal and providing said second component signal of said second subarray signal; and
    a control circuit for supplying said first and second control signals to said first and second variable amplitude circuits, respectively, in response to said phase shift value.

12. An ultrasound imaging system as defined in claim 9 wherein said phase shift network comprises a first phase shifter for phase shifting said first subarray signal to provide a first phase shifted signal, a second phase shifter for phase shifting said second subarray signal to provide a second phase shifted signal and a summer for summing said first and second phase shifted signals to provide said phase shifted subarray signal.

13. An ultrasound imaging system as defined in claim 9 comprising a transducer assembly and an electronics unit, said transducer assembly comprising a transducer handle containing said array of transducer elements and said subarray processors, a transducer connector for connecting said transducer assembly to said electronics unit and a transducer cable interconnecting said transducer handle and said transducer connector.

14. An ultrasound imaging system as defined in claim 9 wherein each of said subarray processors further comprises registers for holding an initial phase shift value and incremental x and y phase shift values and wherein each of the receive elements of the array has an associated adder for determining an element phase shift value in response to said initial phase shift value and said incremental phase shift values.

15. An ultrasound imaging system as defined in claim 9 wherein said transducer includes separate transmit and receive elements.

16. An ultrasound imaging system as defined in claim 9 wherein the transducer elements of said array transmit and receive ultrasound energy.

17. An ultrasound imaging system as defined in claim 9 wherein said transmitter comprises transmit circuitry associated with each of said subarrays and wherein said transmit circuitry is a part of said subarray processor.

18. An ultrasound imaging system as defined in claim 17 wherein said subarray processors, including said transmit circuitry and said receive circuitry, are located with said transducer in a transducer handle.

19. An ultrasound imaging system as defined in claim 9 wherein said primary beamformer includes means for processing said phase shifted subarray signals to provide two or more receive beams simultaneously.

20. An ultrasound imaging system as defined in claim 9 wherein each subarray processor includes means for controlling said first and second component signals in response to phase shift values representative of a desired steering angle of the respective subarray.

21. An ultrasound imaging system as defined in claim 9 wherein said primary beamformer has a plurality of channels and wherein said imaging system further comprises electronic switches for selectively connecting different ones of said phase shifted subarray signals to said primary beamformer channels, wherein an active aperture is electronically moved with respect to said array.

22. An ultrasound imaging system as defined in claim 21 wherein said array has a linear or curved linear geometry and wherein the active aperture is electronically moved along the length of the array.

23. An ultrasound imaging system comprising:
    a two-dimensional array of ultrasound transducer elements that define a plurality of subarrays:
    a transmitter for transmitting ultrasound energy into a region of interest along a desired scan line in a three-dimensional space with transmit elements of the array;
    a subarray processor associated with each of said subarrays, each subarray processor comprising receive circuitry, responsive to transducer signals generated by receive elements of the associated subarray in response to ultrasound energy received from said region of interest, for providing first and second subarray signals, said first subarray signal comprising a sum of first weighted component signals and said second subarray signal comprising a sum of second weighted component signals, said first and second component signals being derived from the respective transducer signals;
    a phase shift network associated with each of said subarrays for phase shifting and combining said first and second subarray signals to provide a phase shifted subarray signal;
    a primary beamformer comprising a delay circuit associated with each of said subarrays for delaying said phase shifted subarray signals by delays that are individually controlled and providing delayed subarray signals, and a summing circuit for summing said delayed subarray signals and providing a beamformer signal; and
    an image generating circuit responsive to said beamformer signal for generating an image of the region of interest, said imaging system comprising a transducer assembly and an electronics unit, said transducer assembly comprising a transducer handle containing said array of transducer elements and said subarray processors, a transducer connector for connecting said transducer assembly to said electronics unit and a transducer cable interconnecting said transducer handle and said transducer connector, wherein said phase shift networks are located in said transducer connector.

24. An ultrasound imaging system comprising:
    a two-dimensional array of ultrasound transducer elements that define a plurality of subarrays;
    a transmitter for transmitting ultrasound energy into a region of interest along a desired scan line in a three-dimensional space with transmit elements of the array;
    a subarray processor associated with each of said subarrays, each subarray processor comprising receive circuitry, responsive to transducer signals generated by receive elements of the associated subarray in response to ultrasound energy received from said region of interest, for providing first and second subarray signals, said first subarray signal comprising a sum of first weighted component signals and said second subarray signal comprising a sum of second weighted component signals, said first and second component signals being derived from the respective transducer signals;

a phase shift network associated with each of said subarrays for phase shifting and combining said first and second subarray signals to provide a phase shifted subarray signal;

a primary beamformer comprising a delay circuit associated with each of said subarrays for delaying said phase shifted subarray signals by delays that are individually controlled and providing delayed subarray signals, and a summing circuit for summing said delayed subarray signals and providing a beamformer signal; and an image generating circuit responsive to said beamformer signal for generating an image of the region of interest, said imaging system comprising a transducer assembly and an electronics unit, said transducer assembly comprising a transducer handle containing said array of transducer elements and said subarray processors, a transducer connector for connecting said transducer assembly to said electronics unit and a transducer cable interconnecting said transducer handle and said transducer connector, wherein said phase shift networks are located in said electronics unit.

25. An ultrasound imaging system comprising:

a two-dimensional array of ultrasound transducer elements that define a plurality of subarrays;

a transmitter for transmitting ultrasound energy into a region of interest along a desired scan line in a three-dimensional space with transmit elements of the array;

a subarray processor associated with each of said subarrays, each subarray processor comprising receive circuitry, responsive to transducer signals generated by receive elements of the associated subarray in response to ultrasound energy received from said region of interest, for providing first and second subarray signals, said first subarray signal comprising a sum of first weighted component signals and said second subarray signal comprising a sum of second weighted component signals, said first and second component signals being derived from the respective transducer signals;

a phase shift network associated with each of said subarrays for phase shifting and combining said first and second subarray signals to provide a phase shifted subarray signal;

a primary beamformer comprising a delay circuit associated with each of said subarrays for delaying said phase shifted subarray signals by delays that are individually controlled and providing delayed subarray signals, and a summing circuit for summing said delayed subarray signals and providing a beamformer signal; and an image generating circuit responsive to said beamformer signal for generating an image of the region of interest, said imaging system comprising a transducer assembly and an electronics unit, said transducer assembly comprising a transducer handle containing said array of transducer elements and said subarray processors, a transducer connector for connecting said transducer assembly to said electronics unit and a transducer cable interconnecting said transducer handle and said transducer connector, wherein said phase shift networks are located in said transducer handle.

26. An ultrasound imaging system comprising:

a two-dimensional array of ultrasound transducer elements that define a plurality of subarrays;

a transmitter for transmitting ultrasound energy into a region of interest along a desired scan line in a three-dimensional space with transmit elements of the array;

a subarray processor associated with each of said subarrays, each subarray processor comprising receive circuitry, responsive to transducer signals received by receive elements of the associated subarray in response to ultrasound energy received from said region of interest, wherein the receive elements of the associated subarray are distributed in at least two dimensions on said two-dimensional array, said receive circuitry providing first and second subarray signals, said first subarray signal comprising a sum of first component signals and said second subarray signal comprising a sum of second component signals, said first and second component signals being derived from the respective transducer signals;

a primary beamformer comprising first and second delay circuits associated with each of said subarrays for delaying said first and second subarray signals, respectively, by delays that are individually controlled and providing delayed subarray signals, and a summing circuit for summing said delayed subarray signals and providing a beamformer signal; and an image generating circuit responsive to said beamformer signal for generating an image of the region of interest.

27. A method for ultrasound imaging comprising the steps of:

providing a two-dimensional array of ultrasound transducer elements that define a plurality of subarrays;

transmitting ultrasound energy into a region of interest along a desired scan line in a three-dimensional space with transmit elements of the array;

receiving ultrasound energy from said region of interest with receive elements of each of said subarrays and generating transducer signals, wherein the receive elements of each of said subarrays are distributed in at least two dimensions on said two-dimensional array;

for each of said subarrays, processing said transducer signals in accordance with a desired operation and providing a phased shifted subarray signal;

delaying each of said phased shifted subarray signals by delays that are individually controlled and providing delayed subarray signals;

summing said delayed subarray signals and providing a beamformer signal; and generating an image of the region of interest in response to said beamformer signal.

28. A method as defined in claim 27 wherein an ultrasound imaging system for performing said method includes a transducer assembly, and wherein the step of processing the respective transducer signals is performed in said transducer assembly.

29. A method as defined in claim 27 wherein the step of processing the respective transducer signals comprises the steps of:

deriving first and second component signals from each of the transducer signals generated by the receive elements of the associated subarray;

weighting each of said first and second component signals in accordance with a desired phase shift;

summing the first weighted component signals to provide a first subarray signal;

summing the second weighted component signals to provide a second subarray signal; and phase shifting and combining said first and second subarray signals to provide said phased shifted subarray signal.

30. A method for ultrasound imaging comprising the steps of:

providing a two-dimensional array of ultrasound transducer elements that define a plurality of subarrays;

transmitting ultrasound energy into a region of interest along a desired scan line in a three-dimensional space with transmit elements of the array;

receiving ultrasound energy from said region of interest with receive elements of each of said subarrays and generating transducer signals, wherein the receive elements of each of said subarrays are distributed in at least two dimensions on said two-dimensional array;

for each of said subarrays, processing the respective transducer signals in accordance with a desired operation and providing first and second subarray signals;

delaying said first and second subarray signals by delays that are individually controlled and providing delayed subarray signals;

summing said delayed subarray signals and providing a beamformer signal; and generating an image of the region of interest in response to said beamformer signal.

* * * * *